United States Patent [19]

Lantzsch et al.

[11] Patent Number: 5,602,282

[45] Date of Patent: Feb. 11, 1997

[54] PROCESS FOR THE PREPARATION OF 2-AMINO-2-ARYLETHANOLS AND NOVEL INTERMEDIATES

[75] Inventors: Reinhard Lantzsch, Wuppertal; Ernst Kysela, Bergisch Gladbach; Albrecht Marhold, Leverkusen, all of Germany

[73] Assignee: Bayer Aktiengesellschaft, Leverkusen, Germany

[21] Appl. No.: 511,207

[22] Filed: Aug. 4, 1995

[30] Foreign Application Priority Data

Aug. 12, 1994 [DE] Germany ............... 44 28 533.7

[51] Int. Cl.$^6$ ................................. C07C 213/00
[52] U.S. Cl. ................ 564/358; 544/335; 546/246; 549/75; 564/337
[58] Field of Search ................ 564/337, 358; 549/75; 546/246; 544/335

[56] References Cited

PUBLICATIONS

Pickle et al. "Improved Chiral Derivatizing Agents, etc" *J. Org. Chem.* vol. 48, No. 15 (1983) 2520–7.

Rosen et al., "Reduction of 2–Indanone Oxime, etc," *J. Org Chem.* vol. 28 (1963), 2797–2804.

Freifelder et al. "Preparation of Cycloheptylamine" *J. Org. Chem.* vol. 27 (1962) 2209

*Primary Examiner*—Peter O'Sullivan
*Attorney, Agent, or Firm*—Sprung Horn Kramer & Woods

[57] ABSTRACT

The invention relates to a novel process for the preparation of 2-amino-2-arylethanols of the formula (I)

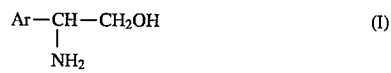

in which

Ar represents aryl or hetaryl each unsubstituted or identically or differently monosubstituted to pentasubstituted, where as substituents there may be mentioned:

halogen, alkyl, halogenoalkyl, alkoxy, halogenoalkoxy, unsubstituted substituted cycloalkyloxy or unsubstituted or substituted phenyl, which comprises catalytically hydrogenating α-hydroxyketoximes of the formula (II)

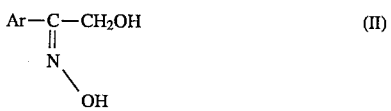

in which

Ar has the meaning given above, using Raney nickel or Raney cobalt in the presence of a diluent and in the presence of a base and novel 2-amino-2-arylethanols and novel α-hydroxyketoximes.

4 Claims, No Drawings

PROCESS FOR THE PREPARATION OF 2-AMINO-2-ARYLETHANOLS AND NOVEL INTERMEDIATES

The invention relates to a novel process for the preparation of novel 2-amino-2-arylethanols and novel intermediates for the preparation thereof.

It is known that 2-amino-2-arylethanols and derivatives thereof are obtained if correspondingly substituted aromatic amino acids or esters thereof or oxime ethers or hydroxy-oximes are reduced by complex metal hydrides such as $NaBH_4/BF_3$ or $LiAlH_4$ (cf. e.g. EP 322982, Z. Anorg. Allg. Chemie 1970, 376, 296–302 or Comprehensive Organic Synthesis, Volume 8, pp. 64ff.). However, the use of these metal hydrides is possible on an industrial scale only to a restricted extent since on the one hand they are highly expensive and on the other hand the reactions require considerable safety expenditure.

It is further known that certain amines can be obtained by catalytic hydrogenation using noble metal catalysts, such as rhodium catalysts or palladium catalysts and in the presence or absence of acids, such as acetic acid, sulfuric acid or hydrochloric acid (cf. e.g. J. Org. Chem. 27, 2209, 1962; J. Org. Chem. 28, 2797, 1963; J. Org. Chem. 48, 2520 (1983). However, these processes have the disadvantage that they cannot be used without restrictions. Thus, for example, using rhodium as catalyst, the reduction of 2-indanone oxime to the corresponding amine does not succeed (cf. Houben-Weyl, Methoden der Organischen Chemie [Methods of Organic Chemistry], Georg Thieme Verlag, Stuttgart, Volume IV, 1c, pages 251–252). Neither can palladium catalysts be used universally, since, for example, the halogen is reductively removed from halogen-substituted aromatics.

The present invention relates to (1) a process for the preparation of 2-amino-2-arylethanols of the formula (I)

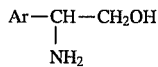

(I)

in which

Ar represents aryl or hetaryl each unsubstituted or identically or differently monosubstituted to pentasubstiuted, where as substituents the may be mentioned: halogen, alkyl, halogenoalkyl, alkoxy, halogenoalkoxy, unsubstituted or substituted cycloalkyloxy or unsubstituted or substituted phenyl, which comprises catalytically hydrogenating α-hydroxyketoximes of the formula (II)

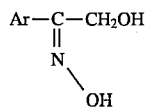

(II)

in which

Ar has the meaning given above, using Raney nickel or Raney cobalt in the presence of a diluent and in the presence of a base;

(2) novel 2-amino-2-arylethanols of the formula (Ia)

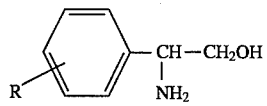

(Ia)

in which

R represents a radical

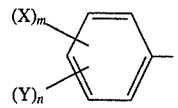

in which

X represents halogen, alkyl or alkoxy,

Y represents halogenoalkoxy or halogen-substituted cycloalkyloxy, m represents the number 0, 1 or 2 and n represents the number 1 or 2;

(3) novel α-hydroxyketoximes of the formula (IIa)

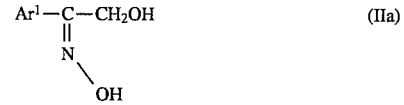

(IIa)

in which $Ar^1$ represents aryl or hetaryl each identically or differently monosubstituted to pentasubstiuted, where as substituents there may be mentioned:
halogen, halogenoalkyl, alkoxy, halogenoalkoxy, unsubstituted or substituted cycloalkoxy or identically or differently monosubstituted to polysubstituted phenyl,
except the compounds 1-(4-methoxyphenyl)-2-hydroxy-ethanone oxime and 1-(5-bromo-2-thienyl)-2-hydroxy-ethanone oxime (Khimiya i Tekhnol, Elementoorg. Poluproduktov i Polimerov, Volgograd (1984) 20–4, from: Ref. Zh., Khim, 1985, Abstr. No. 9Zh241; Huaxue Xuebao (1983), 41(4), 380–4, CODEN: HHHPA4; ISSN: 0567-7351).

It is considered to be extremely surprising that the 2-amino-2-arylethanols of the formula (I) are obtained in very good yields and in high purity by the process (1) according to the invention, since it is known that in the catalytic hydrogenation of ketoximes and use of platinum catalysts or Raney nickel catalysts hydroxylamines result [Houben-Weyl, Methoden der Organischen Chemie [Methods of Organic Chemistry], Georg Thieme Verlag, Stuttgart, Volume IV, 1c, Part 1, page 251; JACS 59, 715 (1937) and Chem. Ber. 88, 38 (1955)]. The process according to the invention for the preparation of the 2-amino-2-arylethanols of the formula (I) described above under (1), in contrast, is broadly applicable and thus represents a valuable enrichment of the art.

By the process according to the invention, compounds of the formula (I) are preferably prepared in which Ar represents in each case identically or differently monosubstituted to pentasubstiuted phenyl or in each case identically or differently monosubstituted to trisubstituted thienyl, pyridyl or pyrimidinyl, where as substituents there may be mentioned in each case:
fluorine, chlorine, bromine, $C_1$–$C_6$-alkyl, $C_1$–$C_6$-halogenoalkyl, $C_1$–$C_6$-alkoxy, $C_{1-C6}$-halogenoalkoxy, $C_3$–$C_6$-cycloalkyloxy unsubstituted or substituted by halogen or $C_{1-C6}$-alkyl, and phenyl unsubstituted or identically or differently monosubstituted to pentasubstituted by fluorine, chlorine, bromine, $C_1$–$C_6$-alkyl, $C_{1-C6}$-halogenoalkyl, $C_1$–$C_6$-alkoxy, $C_1$–$C_6$-halogenoalkoxy or $C_3$–$C_6$cycloalkyloxy unsubstituted or substituted by halogen or $C_1$–$C_6$-alkyl.

By the process according to the invention, compounds of the formula (I) are particularly preferably prepared in which represents in each case identically or differently monosubstituted to trisubstituted phenyl, thienyl, pyridyl or pyrimidinyl, where as substituents there may be mentioned:

fluorine, chlorine, bromine, $C_1$–$C_4$-alkyl, $C_1$–$C_4$-halogenoalkyl, $C_1$–$C_4$-alkoxy, $C_1C_4$-halogenoalkoxy, $C_3$–$C_6$-cycloalkyloxy unsubstituted or substituted by halogen, and phenyl unsubstituted or identically or differently monosubstituted to trisubstituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy or $C_3$–$C_6$-cycloalkyloxy unsubstituted or substituted by halogen.

By the process according to the invention, compounds of the formula (I) are very particularly preferably prepared in which Ar represents identically or differently monosubstituted or disubstituted phenyl, where as substituents there may be mentioned: fluorine, chlorine, bromine, $C_1$–$C_4$-alkyl unsubstituted or substituted by fluorine and/or chlorine, $C_1$–$C_4$-alkoxy unsubstituted or substituted by fluorine and/or chlorine, $C_3$–$C_6$-cycloalkyloxy unsubstituted or monosubstituted or polysubstituted by fluorine and/or chlorine and phenyl unsubstituted or identically or differently monosubstituted or disubstituted by fluorine, chlorine, bromine, $C_1$–$C_4$-alkyl unsubstituted or substituted by fluorine and/or chlorine, $C_1$–$C_4$-alkoxy unsubstituted or substituted by fluorine and/or chlorine or $C_3$–$C_6$-cycloalkyloxy unsubstituted or monosubstituted or polysubstituted by fluorine and/or chlorine.

The general radical definitions or radical definitions specified in preferred ranges listed above apply both to the end products of the formula (I) and correspondingly to the starting materials and/or intermediates required in each case for the preparation.

These radical definitions can be combined together in any manner, that is also between the respective ranges and preferred ranges.

If for example, the oxime of 4-difluoromethoxy-ω-hydroxy-acetophenone as starting material, hydrogen and Raney nickel as catalyst are used, the come of the reaction of the process according to the invention may be depicted by the following equation:

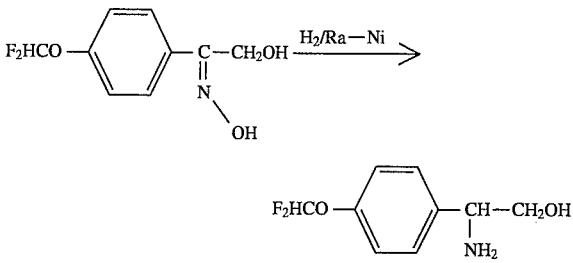

The α-hydroxyketoximes to be used as starting materials for the preparation of the compounds of the formula (I) in the process according to the invention specified under (I) are generally defined by the formula (II). In formula (II), Ar preferably represents or particularly preferably represents those meanings which have already been specified above as preferred or particularly preferred for Ar in connection with the description of the compounds of the formula (I).

Some of the αhydroxyketoximes of the formula (II) are known (cf. e.g. J. Chem. Technol. Biotechnol., 54(1), 19–26, 1992).

However, still unknown and likewise subject-matter of this invention are the αhydroxyetoximes specified above under (3) and defined by the formula (IIa).

$Ar^1$ perferably represents identically or differently monosubstituted to pentasubstiuted phenyl or in each case identically or differently monosubstituted to trisubstituted thienyl, pyridyl or pyrimidinyl, where as substituents there may be mentioned:

fluorine, chlorine, bromine, $C_2$–$C_6$-alkoxy, $C_1$–$C_6$-halogenoalkoxy, $C_3$–$C_6$-cycloalkyloxy unsubstituted or substituted by halogen or $C_1$–$C_6$-alkyl, and phenyl unsubstituted or identically or differently monosubstituted to pentasubstituted by fluorine, chlorine, bromine, $C_1$–$C_6$-alkyl, $C_1$–$C_6$-alkoxy, $C_1$–$C_6$-halogenoalkoxy or $C_3$–$C_6$-cycloalkyloxy unsubstituted or substituted by halogen or $C_1$–$C_6$-alkyl.

$Ar^1$ particularly preferably represents in each case identically or differently monosubstituted to trisubstituted phenyl, thienyl, pyridyl or pyrimidinyl, where as substituents there may be mentioned:

fluorine, chlorine, bromine, $C_2$–$C_4$-alkoxy, $C_1$–$C_4$-halogenoalkoxy, $C_3$–$C_6$-cycloalkyloxy unsubstituted or substituted by halogen and phenyl identically or differently monosubstituted to trisubstituted by fluorine, chlorine, bromine, $C_1$–$C_4$-alkyl, $C_1$–$C_4$-alkoxy, $C_1$–$C_4$-halogenoalkoxy or $C_3$–$C_6$-cycloalkyloxy unsubstituted or substituted by halogen.

$Ar^1$ very particularly preferably represents identically or differently monosubstituted or disubstituted phenyl, where as substituents them may be mentioned:

fluorine, chlorine, bromine, $C_2$–$C_4$-alkoxy, $C_1$–$C_4$-alkoxy substituted by fluorine and/or chlorine, $C_3$–$C_6$-cycloalkyloxy unsubstituted or monosubstituted or polysubstituted by fluorine and/or chlorine, and phenyl identically or differently monosubstituted or disubstituted by fluorine, chlorine, bromine, $C_1$–$C_4$-alkyl, $C_1$–$C_4$-alkoxy unsubstituted or substituted by fluorine and/or chlorine or $C_3$–$C_6$-cycloalkyloxy unsubstituted or monosubstituted or polysubstituted by fluorine and/or chlorine.

The compounds 1-(4-methoxyphenyl)-2-hydroxy-ethanone oxime and 1-(5-bromo-2-thienyl) -2-hydroxy-ethanone oxime (Khimiya i Tekhnol, Elementoorg. Poluproduktov i Polimerov, Volgograd (1984) 200-4, from: Ref. Zh., Khim, 1985, Abstr. No. 9Zh241; Huaxue Xuebao (1983), 41(4), 380-4, CODEN: HHHPA4;ISSN: 0567–7351) are excluded from each of these definitions.

The known and also the novel compounds of the formula (II) can be obtained by generally known processes and in a conventional manner from the corresponding ω-hydroxyketones and hydroxylamine hydrochloride (cf. Preparation Example).

The ω-hydroketones are obtained, for example, by reacting the corresponding ω-chloroketones, which in turn are obtainable, for example, by Friedel-Crafts acylation of substituted benzenes with chloroacetyl chloride in the presence of aluminum chloride, with salts of formic acid (cf. the Preparation Examples).

The process described under (1) is carried out in the presence of Raney nickel or Raney cobalt. These are well-known catalysts which are described, e.g. in Houben-Weyl, Methoden der Organischen Chemie [Methods of Organic Chemistry], Georg Thieme Verlag, Stuttgart, Volume 4/1c (Reductions) pp. 18 ff.

The process according to the invention described under (1) is preferably carried out in the presence of a diluent.

Diluents which are useful are all conventional organic solvents inert under the reaction conditions. These include alcohols, such as methanol, ethanol, n-propanol, iso-propanol, n-butanol or iso-butanol; hydrocarbons, such as benzene, toluene, xylene, hexane, cyclohexane or ethers, such as diethyl ether, diisopropyl ether, tert-butyl methyl ether, tert-amyl methyl ether, 1,2-dimethoxyethane, tetrahydrofuran and dioxane.

However, under the reaction conditions it can also be advantageous to use mixtures of water and one of the diluents specified above.

The reaction temperatures can be varied in a relatively broad range when the process according to the invention described under (1) is carried out. Generally, temperatures between 15° C. and 180° C. are employed, preferably temperatures between 30° C. and 120° C.

The process according to the invention described under (1) is carried out in the presence of hydrogen and generally under pressure, the hydrogen pressure being between one and 150 bar, preferably between 15 and 100 bar.

The process according to the invention described under (1) is carried out under basic reaction conditions, preferably in the presence of ammonia. This can be used if appropriate in the gaseous or liquid state.

1 to 100 equivalents, preferably 5 to 50 equivalents, of ammonia and 1 to 150 percent by weight, preferably 10 to 60 percent by weight of Raney nickel or Raney cobalt am used per, for example, 1 mol of α-hydroxyketoxime of the formula (II).

The work-up can proceed by conventional methods, for example by filtering off the catalyst and removing the solvent under reduced pressure. The crude product thus obtained can be purified by recrystallization or chromatography. The amino alcohols can also be purified by formation of their salts, e.g. the hydrochlorides.

The 2-amino-2-arylethanols specified above under (2) are generally defined by the formula (Ia). For this formula, the following applies: for m =2 or n=2, the radicals X or Y, respectively, can be identical or different.

In the radical R of the formula (Ia)

X preferably represents fluorine, chlorine, bromine, $C_1$–$C_4$-alkyl or $C_1$–$C_4$-alkoxy, Y preferably represents $C_1$–$C_4$-halogenoalkoxy or halogen-substituted $C_3C_6$-cycloalkoxy, n preferably represents the number 1 and m preferably represents 0 or 1.

Particular preference is given to compounds of the formula (a) in which

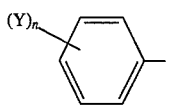

R represents a radical
in which
Y represents fluorine- and/or chlorine-substituted $C_1$–$C_4$-alkoxy or fluorine- and/or chlorine-substituted $C_3$–$C_6$-cycloalkoxy and n represents the number 1.

Very, particular preference is given to compounds of the formula (Ia) in which

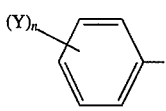

R represents a radical
in which
Y represents one of the following radicals:
—$OCHF_2$, —$OCClF_2$, —$OCF_2CHFCl$, —$OCF_2CH_2F$, —$OCF_2CHF_2$, —$OCF_2CCl_3$, —$OCF_2CHFCF_3$, —$OCH_2CF_3$, —$OCH_2CF_2CHF_2$, —$OCH_2CF_2CF_3$,

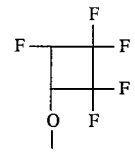

or

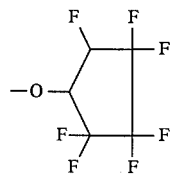

and n represents the number 1.

The 2-amino-2-arylethanols of the formula (Ia) are novel and are subject-matter of the invention. They can be obtained by the process (1) according to the invention.

The 2-amino-2-arylethanols of the formula (I) to be prepared by the process according to the invention can be used as starting materials for the preparation of pesticides (cf. e.g. EP 432661 ).

PREPARATION EXAMPLES

Example 1

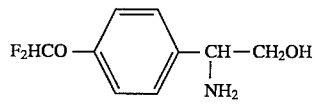

9.8 g (0.045 mol) of 2-hydroxy-1-(4-difluoromethoxyphenyl)-ethanone oxime in 100 ml of methanol, 25 ml of liquid ammonia and 5 g of Raney nickel are hydrogenated at 50° C. and a hydrogen pressure of 60 to 70 bar until no more hydrogen is absorbed. After the mixture is cooled, it is depressurized, filtered and the solvent is removed under reduced pressure. A dark oil remains which slowly crystallizes.

7.8 g (84.5% of theory) of 2-amino-2-(4-difluoromethoxyphenyl)-ethanol are obtained having a purity of >99% by gas chromatography) and a melting point of 54°–57° C.

In a similar manner and according to the general specifications for preparation, the compounds of the formula (I) listed below in Table 1 are obtained:

TABLE 1

| Example number | Ar | m.p. [°C.] | Yield % of theory |
|---|---|---|---|
| 2 | F$_2$HCO—⟨C$_6$H$_4$⟩—⟨C$_6$H$_4$⟩— | 127–128 | 67 |
| 3 | (CH$_3$)$_3$C—⟨C$_6$H$_4$⟩— | 98 | 81 |
| 4 | Cl—⟨C$_6$H$_4$⟩—⟨C$_6$H$_4$⟩— | 82 (decomposes) | 89 |
| 5 | F$_3$CO—⟨C$_6$H$_4$⟩—⟨C$_6$H$_4$⟩— | 124 | 78 |
| 6 | (CH$_3$)$_3$C—⟨C$_6$H$_3$(OC$_2$H$_5$)⟩— | 78 | 85 |
| 7 | CF$_3$—CHF—CF$_2$—O—⟨C$_6$H$_4$⟩—⟨C$_6$H$_4$⟩— | 154 | 68 |
| 8 | ClFHC—CF$_2$—O—⟨C$_6$H$_4$⟩—⟨C$_6$H$_4$⟩— | 136 | 71 |
| 9 | CF$_2$HCF$_2$O—⟨C$_6$H$_4$⟩—⟨C$_6$H$_4$⟩— | 130 | 88 |

Preparation of the starting materials

EXAMPLE (II-1)

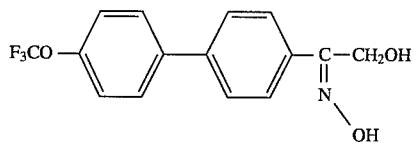

5.9 g (0.02 mol) of 4-trifluoromethoxyphenyl-ω-hydroxy-acetophenone are introduced in 50 ml of dimethoxyethane, 5 ml of water are added, followed by 2.1 g (0.025 mol) of sodium acetate and 1.7 g (0.025 mol) of hydroxylamine hydrochloride, and the mixture is stirred for 12 hours at room temperature. The mixture is poured onto ice-water and filtered.

Yield: 5.9 g (88% of theory) Melting point 150–157° C. (E/Z: 25:75)

By analog with Example II-1 and in accordance with the general specifications for preparation, the compounds of the formula (II) listed below in Table 2 are obtained:

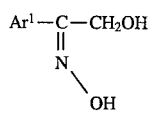

TABLE 2

| Example number | Ar | m.p. |
|---|---|---|
| (II-2) | F$_2$HC—O—⟨C$_6$H$_4$⟩—⟨C$_6$H$_4$⟩— | 162–168° C. (decomposes) |
| (II-3) | (CH$_3$)$_3$C—⟨C$_6$H$_4$⟩— | 128–132° C. |
| (II-4) | Cl—⟨C$_6$H$_4$⟩—⟨C$_6$H$_4$⟩— | 152–154° C. |

TABLE 2-continued

| Example number | Ar | m.p. |
|---|---|---|
| (II-5) | 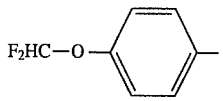 | 66–72° C. |
| (II-6) | 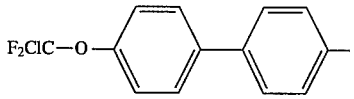 | 152–157° C. |

Example of the preparation of an ω-hydroxyacetophenone

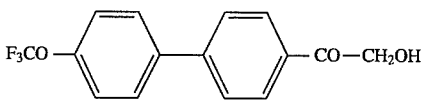

6.75 g (0.0215 mol) of 4-trifluoromethoxyphenyl-ω-chloroacetophenone are suspended in ethanol/water and 9.2 g (0.1358 tool) of sodium formate are added. The mixture is heated to boiling for 12 hours, the ethanol is substantially distilled off, and the mixture is diluted with water and filtered.

6.5 g of beige crystals (90% of theory) are obtained having a melting point of 165° C.

Example of the preparation of an
- ω-chloroacetophenone

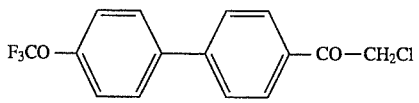

7 g (0.0525 mol) of aluminum chloride are introduced in 50 ml of 1,2-dichloroethane. 5.9 g (0.0525 mol) of chloroacetyl chloride are added dropwise at 5 to 10° C. and then 11.9 g (0.05 mol) of 4-trifluoromethoxybiphenyl are added in portions at −10° C. The mixture is further stirred for 12 hours at room temperature, the reaction mixture is poured onto ice-water and extracted with ethyl acetate. The organic phase is separated off, washed once with sodium bicarbonate solution and twice with water, dried and concentrated.

14.3 g of crude product are obtained which is purified on a silica gel column (mobile phase: methylene chloride). 6.85 g of light beige crystals are obtained having a melting point of 74°–76° C. Yield: 38.5% of theory.

What is claimed is:

1. A process for the preparation of compounds of the formula (I)

in which

Ar represents aryl or hetaryl each unsubstituted or identically or differently monosubstituted to pentasubstituted, by:

halogen, alkyl, halogenoalkyl, alkoxy, halogenoalkoxy, unsubstituted or substituted cycloalkyloxy or unsubstituted or substituted phenyl, which comprises catalytically hydrogenating compounds of the formula (II)

in which

Ar has the meaning given above, using Raney nickel or Raney cobalt in the presence of a diluent and in the presence of a base.

2. The process for the preparation of compounds of the formula (I) as claimed in claim 1, in which Ar represents in each case identically or differently monosubstituted to pentasubstituted phenyl or in each case identically or differently monosubstituted to trisubstituted thienyl, pyridyl or pyrimidinyl, where the substituents are in each case:

fluorine, chlorine, bromine, $C_1$–$C_6$-alkyl, $C_1$–$C_6$-halogenoalkyl, $C_1$–$C_6$-alkoxy, $C_1$–$C_6$-halogenoalkoxy, $C_3$–$C_6$-cycloalkyloxy unsubstituted or substituted by halogen or $C_1$–$C_6$-alkyl, and phenyl unsubstituted or identically or differently monosubstituted to pentasubstituted by fluorine, chlorine, bromine, $C_1$–$C_6$-alkyl, $C_1$–$C_6$-halogenoalkyl, $C_1$–$C_6$-alkoxy, $C_1$–$C_6$-halogenoalkoxy or $C_3$–$C_6$-cycloalkyloxy unsubstituted or substituted by halogen or $C_1$–$C_6$-alkyl.

3. The process for the preparation of compounds of the formula (I) as claimed in claim 1, in which Ar represents in each case identically or differently monosubstituted to trisubstituted phenyl, thienyl, pyridyl or pyrimidinyl, where the substituents are in each case:

fluorine, chlorine, bromine, $C_1$–$C_4$-alkyl, $C_1$–$C_4$-halogenoalkyl, $C_1$–$C_4$alkoxy, $C_1$–$C_4$-halogenoalkoxy, $C_3$–$C_6$-cycloalkyloxy unsubstituted or substituted by halogen, and phenyl unsubstituted or identically or differently monosubstituted to trisubstituted by fluorine, chlorine, bromine, $C_1$–$C_4$-alkyl, $C_1$–$C_4$-halogenoalkyl, $C_1$–$C_4$-alkoxy, $C_1$–$C_4$halogenoalkoxy or $C_3$–$C_6$-cycloalkyloxy unsubstituted or substituted by halogen.

4. The process for the preparation of compounds of the formula (I) as claimed in claim 1, in which Ar represents identically or differently monosubstituted or disubstituted phenyl, where the substituents are in each case: fluorine, chlorine, bromine, $C_1$–$C_4$-alkyl unsubstituted or substituted by fluorine and/or chlorine, $C_1$–$C_4$-alkoxy unsubstituted or substituted by fluorine and/or chlorine, $C_1$–$C_6$-cycloalkyloxy unsubstituted or monosubstituted or polysubstituted by fluorine and/or chlorine and phenyl unsubstituted or identically or differently monosubstituted or disubstituted by fluorine, chlorine, bromine, $C_1$–$C_4$-alkyl unsubstituted or substituted by fluorine and/or chlorine, $C_1$–$C_4$-alkoxy unsubstituted or substituted by fluorine and/or chlorine or $C_3$–$C_6$-cycloalkyloxy unsubstituted or monosubstituted or polysubstituted by fluorine and/or chlorine.

* * * * *

UNITED STATES PATENT AND TRADEMARK OFFICE
CERTIFICATE OF CORRECTION

PATENT NO. : 5,602,282
DATED : February 11, 1997
INVENTOR(S) : Lantzsch, et al.

It is certified that error appears in the above-indentified patent and that said Letters Patent is hereby corrected as shown below:

Col. 10, line 56   Delete " $C_1-C_6$-cycloalkyloxy " and substitute -- $C_3-C_6$-cycloalkyloxy --

Signed and Sealed this

First Day of July, 1997

Attest:

BRUCE LEHMAN

*Attesting Officer*    *Commissioner of Patents and Trademarks*